(12) United States Patent
Zureikat

(10) Patent No.: US 12,049,584 B2
(45) Date of Patent: Jul. 30, 2024

(54) COMPOSITION AND METHOD FOR PRODUCING THE SENSORY STIMULANT

(71) Applicant: Sabine Zureikat, Amman (JO)

(72) Inventor: Sabine Zureikat, Amman (JO)

(*) Notice: Subject to any disclaimer, the term of this patent is extended or adjusted under 35 U.S.C. 154(b) by 646 days.

(21) Appl. No.: 16/356,355

(22) Filed: Mar. 18, 2019

(65) Prior Publication Data

US 2020/0299559 A1    Sep. 24, 2020

(51) Int. Cl.
  *C09K 5/06* (2006.01)
(52) U.S. Cl.
  CPC ..................... *C09K 5/066* (2013.01)
(58) Field of Classification Search
  None
  See application file for complete search history.

(56) References Cited

U.S. PATENT DOCUMENTS

| | | | | |
|---|---|---|---|---|
| 3,640,756 A * | 2/1972 | Beersma | ..................... | C09J 7/32 428/350 |
| 3,957,472 A * | 5/1976 | Donnelly | .................. | F25D 5/02 62/4 |
| 4,029,759 A * | 6/1977 | Humbert | ................ | A61K 8/345 131/275 |
| 4,062,799 A * | 12/1977 | Matsukawa | .............. | B01J 13/10 264/4.4 |
| 4,081,256 A * | 3/1978 | Donnelly | .................. | F25D 5/02 62/4 |
| 4,920,963 A * | 5/1990 | Brader | ..................... | A61F 7/106 607/109 |
| 5,455,066 A * | 10/1995 | Broich | ................. | C09J 189/005 427/364 |
| 6,146,661 A * | 11/2000 | Hoshino | .............. | A61K 9/0056 424/464 |
| 6,231,702 B1 * | 5/2001 | Blomquist | .............. | C06B 23/04 149/46 |
| 6,893,455 B1 * | 5/2005 | Rafferty | ..................... | A61F 7/02 607/108 |
| 7,189,415 B2 * | 3/2007 | Takagi | ................. | A61K 9/2009 424/466 |
| 7,803,353 B2 * | 9/2010 | Lee | .......................... | A61K 8/34 424/53 |
| 8,795,834 B2 * | 8/2014 | Tetrault | .................... | B01J 20/26 428/407 |
| 9,764,034 B2 * | 9/2017 | Iyoha | ................... | A61K 31/055 |

(Continued)

*Primary Examiner* — Kevin R Kruer
(74) *Attorney, Agent, or Firm* — Pierson IP, PLLC

(57) ABSTRACT

The present invention discloses a composition and method for producing a sensory stimulant. The sensory stimulant composition, comprises at least one cooling agent. The cooling agent comprises urea and ammonium nitrate. The composition further comprises fillers, colorants, carbohydrates, and pharmaceutically acceptable salts. The composition can be coated with, but not limited to, casein film. The composition is configured to indicate the overflow of bodily fluids by providing a cooling effect. The composition is configured to dissolve in liquid, water or blood by withdrawing heat from a surrounding environment and attains the chilling sensation by up to 30° C. temperature drop. The composition could be used in application such as band-aids, surgical pads, self-curing gel, post baby delivery cooling pad, breast feeding bras, gym sweat pads, military vests, daily use pads (panty-liners), sanitary pads and tampons.

2 Claims, 6 Drawing Sheets

(56) References Cited

U.S. PATENT DOCUMENTS

| | | | |
|---|---|---|---|
| 9,879,897 B2* | 1/2018 | Leavitt | F25D 5/02 |
| 10,155,698 B2* | 12/2018 | Leavitt | C05B 7/00 |
| 10,557,659 B2* | 2/2020 | Leavitt | B01F 23/20 |
| 2003/0130636 A1* | 7/2003 | Brock | A61F 13/8405 604/385.01 |
| 2003/0139291 A1* | 7/2003 | Qin | A61L 15/20 502/402 |
| 2004/0141927 A1* | 7/2004 | Johnson | A23G 3/36 424/48 |
| 2004/0247743 A1* | 12/2004 | Wolf | A23G 4/20 426/3 |
| 2005/0095289 A1* | 5/2005 | Takagi | A61K 9/2009 424/464 |
| 2005/0260266 A1* | 11/2005 | Gebreselassie | A61K 8/11 424/468 |
| 2006/0062811 A1* | 3/2006 | Szymczak | A61P 11/14 424/488 |
| 2006/0142713 A1* | 6/2006 | Long | A61F 13/42 604/374 |
| 2006/0142714 A1* | 6/2006 | Jackson | A61L 15/56 604/364 |
| 2006/0280852 A1* | 12/2006 | Harvey | A23G 4/06 426/534 |
| 2007/0014856 A1* | 1/2007 | Takagi | A61K 9/2018 424/464 |
| 2007/0027415 A1* | 2/2007 | Kopreski | A61F 15/02 602/2 |
| 2007/0178123 A1* | 8/2007 | Levenson | A61K 9/0058 424/725 |
| 2008/0045913 A1* | 2/2008 | Johnson | A61F 13/42 604/364 |
| 2008/0147153 A1* | 6/2008 | Quincy | C09K 5/18 607/114 |
| 2009/0155325 A1* | 6/2009 | Wenzel | A61F 13/8405 514/769 |
| 2009/0276018 A1* | 11/2009 | Brader | A61F 7/10 607/104 |
| 2010/0216830 A1* | 8/2010 | Iyoha | A61K 47/26 514/738 |
| 2011/0022137 A1* | 1/2011 | Ennis-Thomas | A62B 17/005 607/108 |
| 2011/0152806 A1* | 6/2011 | Zhou | A61F 13/42 604/366 |
| 2011/0152816 A1* | 6/2011 | Zhou | A61F 13/42 604/385.01 |
| 2011/0178487 A1* | 7/2011 | Noda | A61L 15/42 604/367 |
| 2012/0138848 A1* | 6/2012 | Leavitt | C09K 5/066 252/69 |
| 2012/0202722 A1* | 8/2012 | Laudenklos | C10M 173/02 508/156 |
| 2012/0263659 A1* | 10/2012 | Subkowski | A61P 13/08 544/298 |
| 2012/0323198 A1* | 12/2012 | Pesce | A61L 15/20 604/367 |
| 2013/0034719 A1* | 2/2013 | Zhou | B32B 27/08 156/324 |
| 2013/0112370 A1* | 5/2013 | Schromm | C05G 3/40 165/86 |
| 2013/0202543 A1* | 8/2013 | Kuper | A61Q 5/00 514/551 |
| 2014/0088532 A1* | 3/2014 | Joseph | C09D 11/50 604/361 |
| 2014/0128945 A1* | 5/2014 | Schoning | A61F 7/03 607/109 |
| 2014/0216061 A1* | 8/2014 | Paul | F25D 5/02 62/4 |
| 2016/0128944 A1* | 5/2016 | Chawrai | A61K 8/11 514/159 |
| 2017/0016664 A1* | 1/2017 | Leavitt | F25D 5/02 |
| 2017/0105877 A1* | 4/2017 | Buteux | A61L 15/42 |
| 2017/0189283 A1* | 7/2017 | Sasaki | A61Q 13/00 |
| 2018/0149402 A1* | 5/2018 | Srivastava | A61F 7/106 |
| 2019/0224051 A1* | 7/2019 | Kutay | A61L 15/42 |
| 2020/0199311 A1* | 6/2020 | Foo | G01N 33/02 |
| 2020/0299559 A1* | 9/2020 | Zureikat | A61L 15/32 |

* cited by examiner

COMPOSITION AND METHOD FOR PRODUCING THE SENSORY STIMULANT

BACKGROUND OF THE INVENTION

A. Technical Field

The present invention generally relates to sensory stimulant composition. Specifically, the present invention relates to a sensory stimulant composition to provide cooling sensation effect.

B. Description of Related Art

Innumerable lives have been lost to hemorrhage, escape of tissue fluids from burned or denuded body surfaces, and infections or toxic effects consequent to contamination of open wounds. Accordingly, a variety of methods have been used to stop or control losses of blood or fluids. However, to control or stop the blood flow, the patient or caregiver must notice or detect the bleeding. For example, if the patient is engaged in entertainment shows, gaming or training, they might be fully immersed in the activity and would not be aware of the surroundings. In such cases, the observers would alert or the patient would notice at a time, which would be late to prevent the life-threatening problems.

Another important issue relating to excretion of fluids is menstrual cycle. Since forever, women have suffered the issue of not knowing exactly when their menstrual cycle starts. Menstrual cycle is highly dependent on a women's diet and stress level, this causes it to fluctuate and starts when least expected. Even when one's cycle is regular, one can never know the precise time the cycle starts. Hence, the only indicator is the feeling of excretion of bodily fluids.

Unfortunately, days before menstrual cycle starts, vaginal excretions (mucous production) increase up to 30 times more than average. The sensation one gets from vaginal excretions is equivalent to menstrual cycle starting, which means one cannot depend on that "feeling" and will need to check multiple times and go through numerous "false alarms" until the period finally starts.

Being unaware of menstrual cycle initiation, or leakage of menstrual blood from tampon or sanitary pad is a great discomfort. Accordingly, the daily use panty liners were invented. Although these liners can prevent menstrual blood from leaking out for few minutes after the cycle first starts, if women don't notice the cycle on time, the thin liner will not be able to hold the gush of blood and leaking is bound to take place. Few prior arts addressing the aforesaid problems by certain compositions and processes are discussed below.

U.S. Pat. No. 3,336,128 discloses a process for coating a plant nutrient with phenol formaldehyde, urea and furfuryl alcohol. The process for the preparation of a plant nutrient composition comprises, water resistant polymer coating by a series of aqueous mineral acid-catalyzed polymerization reactions between phenol, formaldehyde, urea and furfuryl alcohol. The proportion of furfuryl alcohol to the other reactants is progressively increased as the polymerization reactions proceed so that the outermost portion of the water-resistant polymer coating contains a higher proportion of furfuryl alcohol than the innermost portion.

US20040234608 discloses rapidly expanding composition for gastric retention and controlled release of therapeutic agents. The composition expands upon contact with gastric fluid and promotes retention of the dosage form in the patient's stomach for a prolonged period of time. The dosage forms are adapted for immediate or controlled release of the active ingredient. The dosage forms may be used advantageously in the treatment of Parkinson's disease with levodopa (L-DOPA) and hyperactivity and attention deficit disorder with methylphenidate.

However, the above discussed prior arts merely mention about the components of the present invention and lacks to provide any knowledge about the cooling effect sensation composition and method to provide alert regarding the overflow of fluid from the user's body or any sources in unusual events.

Hence, there is a need for a composition that would alert the user regarding the overflow of fluid from the user's body. Therefore, the present invention provides a composition comprising of agents that provide a cooling sensation to alert the user from the overflow of bodily fluid. The present invention also provides a method to provide alert regarding the overflow of fluid from the user's body or any sources in unusual events. Further, the present invention provides a basic system comprised of a cooling agent composition that can have an enhanced selectivity towards specific bodily fluids, through the introduction of a coating solution.

SUMMARY OF THE INVENTION

The present invention discloses a composition and method for producing a sensory stimulant. The sensory stimulant composition is provided for application to the skin or in proximity to the skin of a mammal, such as a human. The composition on exposure to fluid such as but not limited to: water, blood, perspiration, urine, etc., starts to dissolve by absorption of heat from the environment and undergoes phase change to provide a significant cooling sensation. The composition is provided in the form, but not limited to pills/gel, that could be used in application such as, but not limited to, band-aids, surgical pads, self-curing gel, post baby delivery cooling pad, breast feeding bras, gym sweat pads, military vests, daily use pads (panty-liners), sanitary pads and tampons.

The sensory stimulant composition, comprises at least one cooling agent. The cooling agent comprises urea, ammonium nitrate or other ammonium salts and a combination herein, resulting in sufficient sensation at all climate setting. The composition further comprises one or more fillers, one or more colorants, one or more carbohydrates, and one or more pharmaceutically acceptable salts, for example, potassium chloride. In another embodiment, the composition comprises at least two cooling components or agents, wherein the cooling agent comprises urea and ammonium nitrate, casein, one or more fillers, one or more colorants, one or more carbohydrates, and one or more pharmaceutically acceptable salts. In one embodiment, the casein is a modified casein. In one embodiment, the carbohydrates include sugar. The composition is configured to indicate the overflow of fluids by providing a cooling effect. The composition is configured to dissolve in some of the body-originating fluid(s), but not limited to, blood, some common solvents, and water, by withdrawing heat from a surrounding environment and attains the chilling sensation by up to 30° C. temperature drop.

In one embodiment, the cooling agent content ranges about 10 wt. % to 94 wt. % of the total composition, the urea content ranges about 62 wt. % to 93.8 wt. % of the total composition, the ammonium nitrate content ranges about 0.1 wt. % to 25 wt. % of the total composition, the potassium chloride content ranges about 1.2 wt. % to 12 wt. % of the total composition and the sugar content ranges of about 2% of the total composition.

In one embodiment, a method of making diffuse phase sensory stimulant formulation is disclosed. The method comprises a step of: melting and cooling ammonium nitrate to form a solid white uniform mass. The method further comprises a step of: pouring a hot melted urea over the uniform mass. The method further comprises a step of: melting the solid ammonium nitrate on penetration of the hot urea. The method further comprises a step of: forming the diffuse phase sensory stimulant formulation. The method further comprises a step of: coating the diffuse phase sensory stimulant formulation with casein film.

In one embodiment, a method of producing casein clay is disclosed. The method comprises a step of: blending modified casein and calcium caseinate with a plasticizer. The method further comprises a step of: modifying the pH in the weak base range to form the casein clay. The method further comprises a step of: adding and stirring silica and talc for rheology. In one embodiment, the pH is modified by adding NaOH. In one embodiment, the plasticizer is oleic acid.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The embodiments herein will be better understood from the following detailed description with reference to the drawings, in which.

DETAILED DESCRIPTION OF EMBODIMENTS

Figure 1:
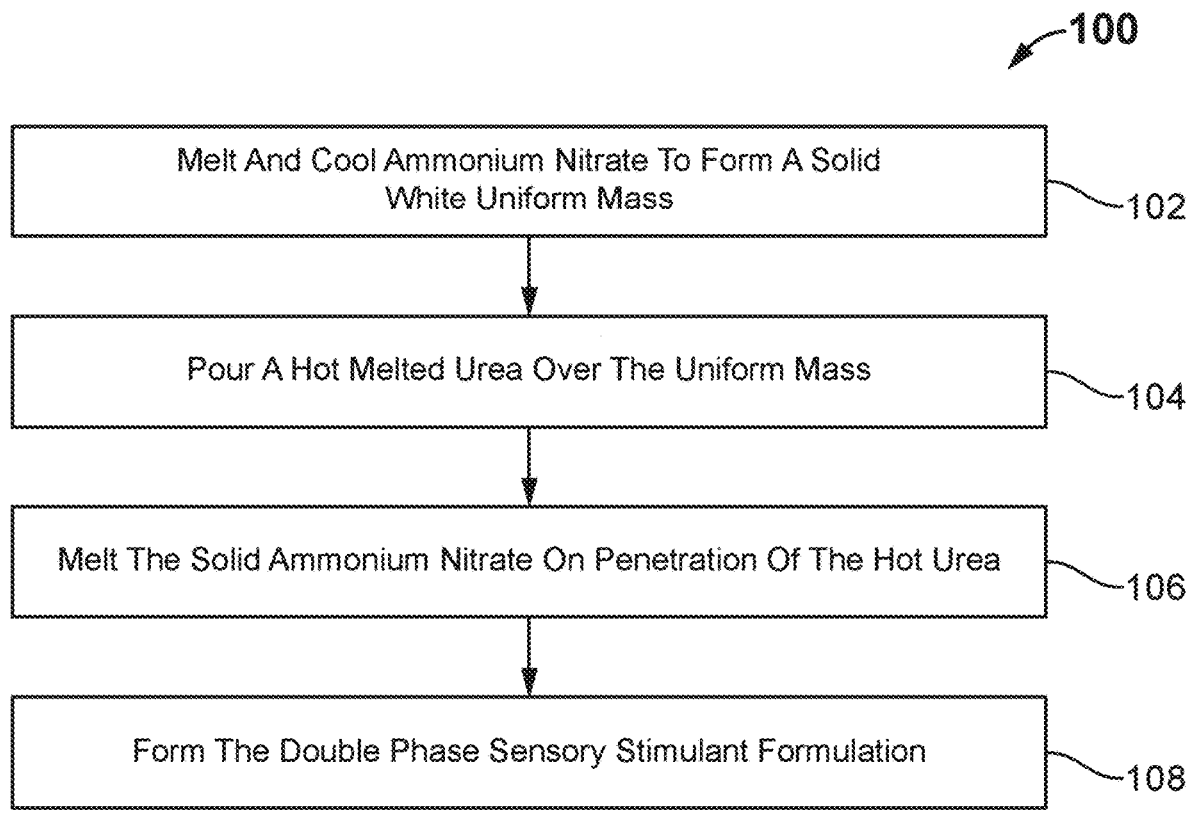
FIG. 1 illustrates a flowchart of a method of making diffuse phase sensory stimulant formulation according to an embodiment of the present invention.

A description of embodiments of the present invention will now be given with reference to the Figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The present invention discloses a composition and method for producing a sensory stimulant. The sensory stimulant composition is configured to dissolve in some of the body-originating fluid(s) but not limited to, blood, water and some common solvents, by withdrawing heat from a surrounding environment and attains the chilling sensation by up to 30° C. temperature drop. The composition is provided in any form, but not limited to, pills/gel, that could be used in application such as band-aids, surgical pads, self-curing gel, post baby delivery cooling pad, breast feeding bras, gym sweat pads, military vests, daily use pads (panty-liners), sanitary pads and tampons. The sensory stimulant composition is provided for application to the skin or in proximity to the skin of a mammal, such as a human. The composition on exposure to fluid such as water, blood, starts to dissolve by absorption of heat from the environment and undergoes phase change to provide a significant cooling sensation.

In one embodiment, the composition comprises one or more cooling components or agents uncoated with casein. In another embodiment, the composition comprises at least two cooling agents, wherein the cooling agent comprises urea and/or ammonium nitrate. The composition further comprises casein, one or more fillers, one or more colorants, one or more carbohydrates, and one or more pharmaceutically acceptable salts. In one embodiment, the cooling agent comprises urea, ammonium nitrate or other ammonium salts and a combination herein. In one embodiment, the casein could be a modified casein. In one embodiment, the salt comprises potassium chloride. Potassium chloride (KCl) is an endothermically dissolving alternative to the table salt. In one embodiment, the composition comprises up to 12% of ammonium nitrate.

In another embodiment, the composition comprises at least one cooling component or agent, wherein the cooling agent comprises urea, casein, one or more fillers, one or more binders, one or more colorants, one or more carbohydrates, and one or more pharmaceutically acceptable salts. In one embodiment, the binder includes magnesium stearate or microcrystalline cellulose. In one embodiment, the carbohydrates include sugar.

In one embodiment, the cooling agent content ranges about 10 wt. % to 94 wt. % of the total composition, the urea content ranges about 62 wt. % to 93.8 wt. % of the total composition, the ammonium nitrate content ranges about 0.1 wt. % to 25 wt. % of the total composition, the potassium chloride content ranges about 1.2 wt. % to 12 wt. % of the total composition and the sugar content ranges of about 2% of the total composition.

In one embodiment, the dissolution of composition comprises two stages. At first stage, the composition generates heat, which is negligible or minor when compared to the temperature drop occurred during the second stage. At second stage, the composition starts dissolving and generates the cooling effect. For example, a 2-gram pill on exposure to enough water or blood, could provide on average 17.9° C. drop from room temperature and the effect sustains till total dissolution of the cooling agent composite in constant fluid flow.

In one embodiment, the sensory stimulant composition comprises at least one form including, but not limited to, prill, double layered pills, dispersed powder, film and film-alike matrices and gel. In another embodiment, the sensory stimulant composition comprises a coin shaped pill form. In one embodiment, the pill is less than 21 mm diameter and 2.5 mm in height. In another embodiment, the pill is less than 1 g in mass. In yet another embodiment, the pill is 0.5 g in mass. In yet another embodiment, the pill is circular in shape. In yet another embodiment, the dimension, shape, color and mass of the pill may vary.

In one embodiment, various method of producing sensory stimulant tablet is disclosed. In one embodiment, the method of making pressed tablet using a rotary tablet press device is disclosed. A batch of hygroscopic urea with tiny amounts (<9 wt. %) of binders, colorant, sugar/KCl, etc., are pressed in the rotary tablet press device or any other suitable device in huge batches, followed by a suitable quality control.

In another embodiment, the method of producing sensory stimulant tablet using melt and cool process is disclosed. The urea and other modifying ingredients are melted together, and the generated liquid is poured in different pill shaped molds or any other molds. In an alternative embodiment, the generated liquid is poured in huge batches for cooling purpose. Then the resulting mass is cut, shaped and polished. In one embodiment, the pill could be porous and lightweight, and bigger in volume. Then the pill is cut to round shape, aiming at 0.8 g or more of raw material, then reducing the thickness by scrubbing and polishing and reaching under 0.5 g. The ratio of the end raw pill comprises a mass different than the one of the solid ingredients mixed together.

In yet another embodiment, the method of producing sensory stimulant tablet using tablet pressing method is disclosed. This method is technologically easiest to induce form and specific dimensions with sufficient reproducibility.

In yet another embodiment, the method of producing sensory stimulant tablet includes growing pill-like crystals in a directed manner, in 2D and 3D grid. In yet another embodiment, the method of producing sensory stimulant tablet includes stacking separate solid layers like a sandwich to form a super pill or double/multi-layered complex pill.

In yet another embodiment, the method of producing double or diffuse phase sensory stimulant tablet is disclosed. Initially, 20% of nitrate is melted and cooled to form a white uniform mass. A layer of hot urea is poured over the uniform mass just when the nitrate is about to totally crystal and solidify. Some of the heat that urea possess melts the solidifying nitrate a bit, and components of each phase penetrate the border of the other, slightly, resulting in a relatively complex biphasic pill. In yet another embodiment, the urea pill and the nitrate pill of sensory stimulant formulation could be combined via glue, starch or by physical manners.

Referring to FIG. 1, the method 100 of making diffuse phase sensory stimulant formulation is disclosed. The method 100 includes a step 102 of: melting and cooling ammonium nitrate to form a solid white uniform mass. The method 100 further includes a step 104 of: pouring a hot melted urea over the uniform mass. The method 100 further includes a step 106 of: melting the solid ammonium nitrate on penetration of the hot urea. The method 100 further includes a step 108 of: forming the diffuse phase sensory stimulant formulation.

In one trail, thermal experiments on 0.5-gram coin sized pill or tablet with NO coat is conducted. For 94%, 92%, 94%, 92%, 92% concentration of urea, 11.6° C., 12.4° C., 10.8° C., 13.3° C., 15.1° C. temperature drops were achieved respectively in 120 seconds, after 3 drops of blood disposed onto the sensory stimulant tablet. In some embodiments, at least 92% of urea generates a drop between 10° C.-15° C. When the composition is incorporated in the pad, the temperature drop was achieved in less than 120 seconds. In one embodiment, the temperature drop could be achieved at different speed, based on the selectivity of the fabric design and/or characteristics of the composition, for example, uncoated composition. In another trial, the temperature drop starts at 10 seconds and reaches 15° C.-20° C. drop in 120 seconds. The speed of the temperature drop is further based on the volume of the fluid such as blood, disposed onto the sensory stimulant tablet.

In one embodiment, the method of preparation of casein film and its composition is disclosed.

Method 1:

A basified emulsion of casein and modifiers is blended with talc and then plasticized with oleic acid. Then, the mixture is dried or dissolved appropriately, and the powder/dissolved mixture is used to mechanically coat polished pills via, for example, pan coater. On a commercial scale, a film coating device can be used to dispense the coating mixture by spraying method. Then the device dries the coating with hot air, so the heat stable casein gently coats the pill. The resultant coating is relatively thin.

In Table 1, a universal pill coating casein system is disclosed.

TABLE 1

| Universal PILL coating CAS system | | |
|---|---|---|
| Name | CAS if present | Wt. % |
| Casein (soluble and hydrophobic combined) | | 6-92% |
| Oleic acid | 112-80-1 | 1-11% |
| Ammonia sol. 10% | 7664-41-7 | 0.2-8.6% |
| Talc | | 2-15% |
| Silica (SiO2) | 7631-86-9 | 0.1-3% |
| Water (deionized) | | To 100% |

Figure 2:
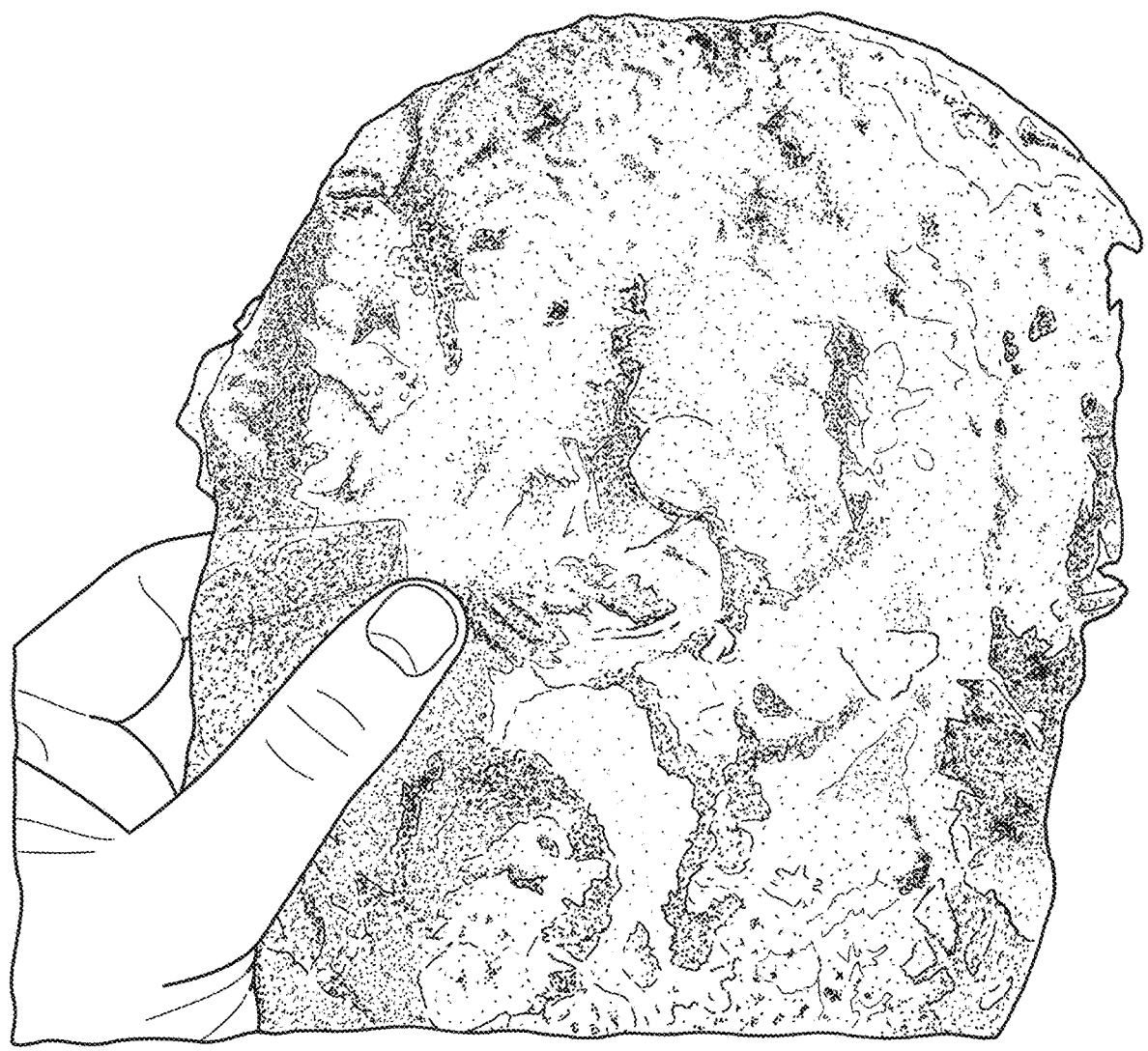
FIG. 2 illustrates a picture of a piece of casein wrap according to an embodiment of the present invention.

In one embodiment, the composition and ranges of the ingredients are used as shown in Table 1. The ingredients of the composition are mixed and stirred constantly. Then, the mixture is left for slow drying at 52° C. for 4 hrs to produce a single film or a powder coat. In one embodiment, coating is of 1 to 9 wt % of pill weight. Further, the coated pill is carefully cured for 11 hrs at 53° C. to make the film, shown FIG. 2. In one embodiment, coating of the tablet of sensory stimulant composition is disclosed. The pill is coated with wet mixture. The coated pill is dried/cured for enwrapping the coating and also for sealing cracks and holes in the crystal matrix of a pill, if present. Further, the composition, may include an assortment, natural flexibility enhancers such as pectin and/or xanthan gum.

Method 2:

In this case, casein, menthol and urea are dissolved in ethanol at different rates. Particularly, casein, originating from, but not limited to, milk and protein shake supplement, are dissolved in ethanol. Then, the resulting mixture is sprayed or brushed on to the pill to form a layer. Then, the pill coated with the layer is dried. In one embodiment, ethanol comprises 85% or higher purity percent. In another embodiment, ethanol comprises 98% or higher purity percent.

Figure 3:
FIG. 3 illustrates a picture of a thin solvent assisted, casein coating according to an embodiment of the present invention.

In one embodiment, modified casein formula is dissolved in 29 grams to 56 grams of solvent, basically 1 g of modified casein formula in at least 29 grams of solvent. In one embodiment, the solvent is anyone of ethanol or acetone. FIG. 3 illustrates a picture of thin solvent-assisted casein film according to an embodiment of the present invention. Ethanol or other organic solvent solutions provide an advantage of operating in almost water free environment.

Figure 4:
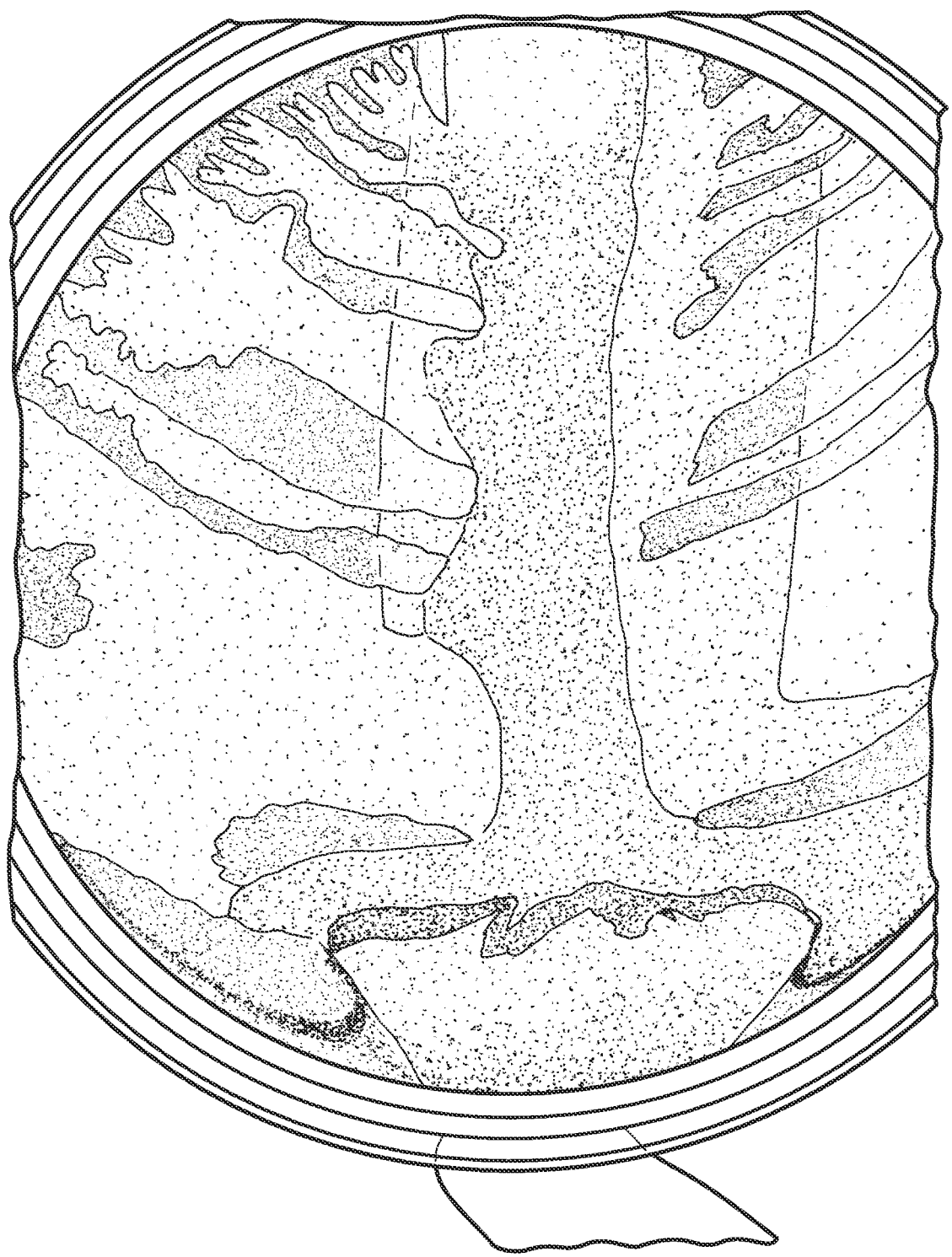
FIG. 4 illustrates a picture of tree shaped casein wrap according to an embodiment of the present invention.

In a system comprising casein to solvent ratio of 1:33, some silica can be sprayed (via spray gun or other suitable device) to form single layer coat on all sides of a pill. Doing it manually requires to dry the pill, which is easily achieved with acetone. So, in hand-mode it's spray top, dry, spray bottom, dry, spray sides, dry and it's ready for use. The resulting film is hydrophobic. Further, the film is in the micrometer (microns) range, so it's not heavy, nor thick and is almost invisible, as shown in FIG. 4. The present invention further provides an option of vacuum station or 'grew' station where pills are soaked in solvent-casein media and after slow evaporation achieves a homogenous coat on the pills. The resulting film, however lacks the surface strength to contain 1 g of urea prills. The film may simply crack due to being thin and not quite flexible.

Method 3:

This technique deploys simple casein installment over urea pill, in solid form, either via regular glue or mechanical impact and also employs curing. This method involves the step of spraying casein powder on top of the pill. Then, the pill is dried in the oven. The micro-melting of urea enables the casein to strongly bound to the urea pill, as the crystallization process would encapsulate the casein 'coat'.

Figure 5:
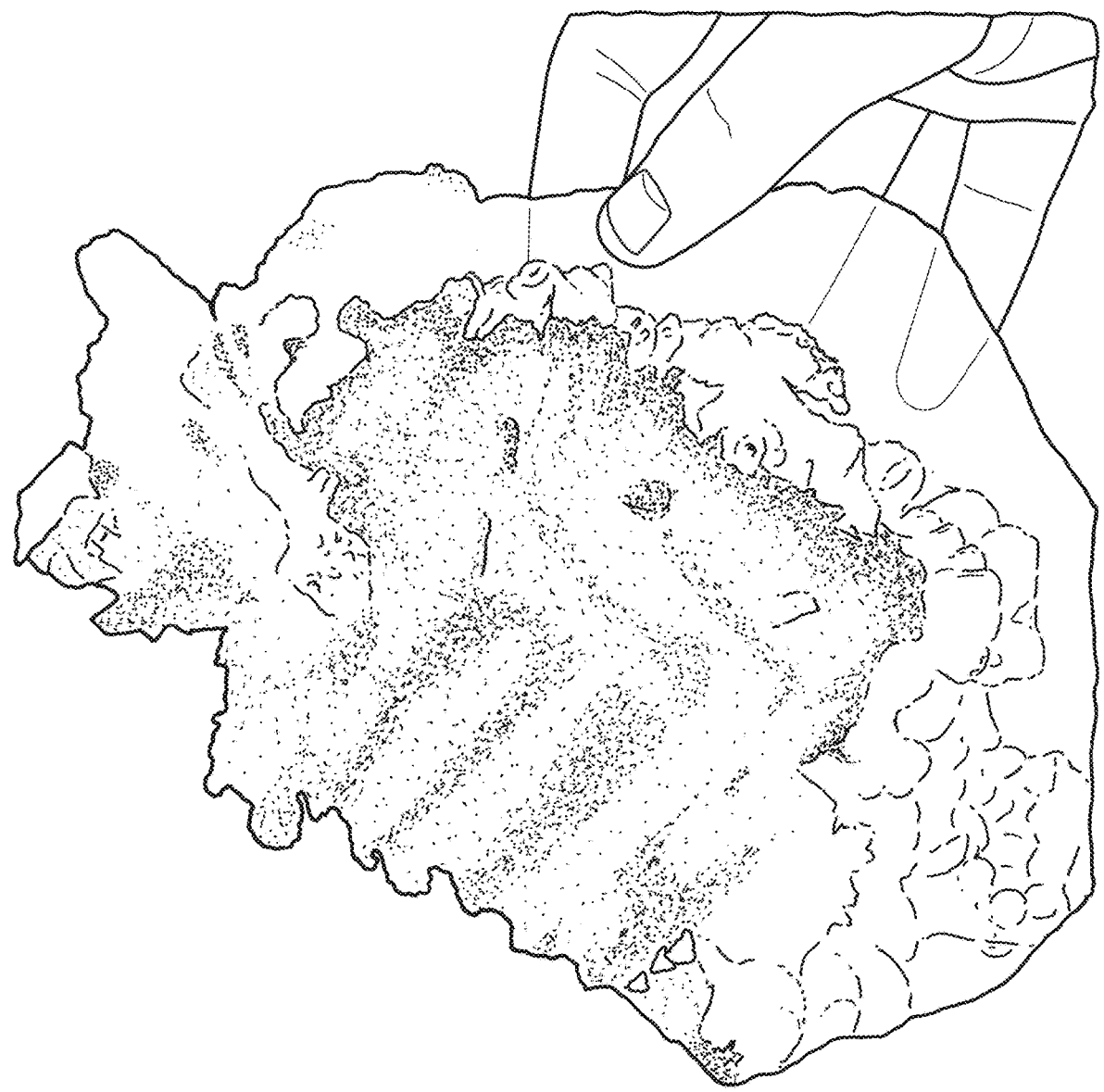
FIG. 5 illustrates a picture of salting and curing of casein film according to an embodiment of the present invention.

In one embodiment, molten solid state to liquid state of urea pill can be 'salted' with acid-casein or prepared 5:2 casein-caseinate mixture. The heat generated from cooling of the melted pill is sufficient to self-cure the powder, as shown in FIG. 5. Same techniques are applicable for applying casein coat or other naturally derived coating alternatives. The resulting coat is uniformly dispersed and qualifies to achieve temperature drop in 70 seconds.

Figure 6:
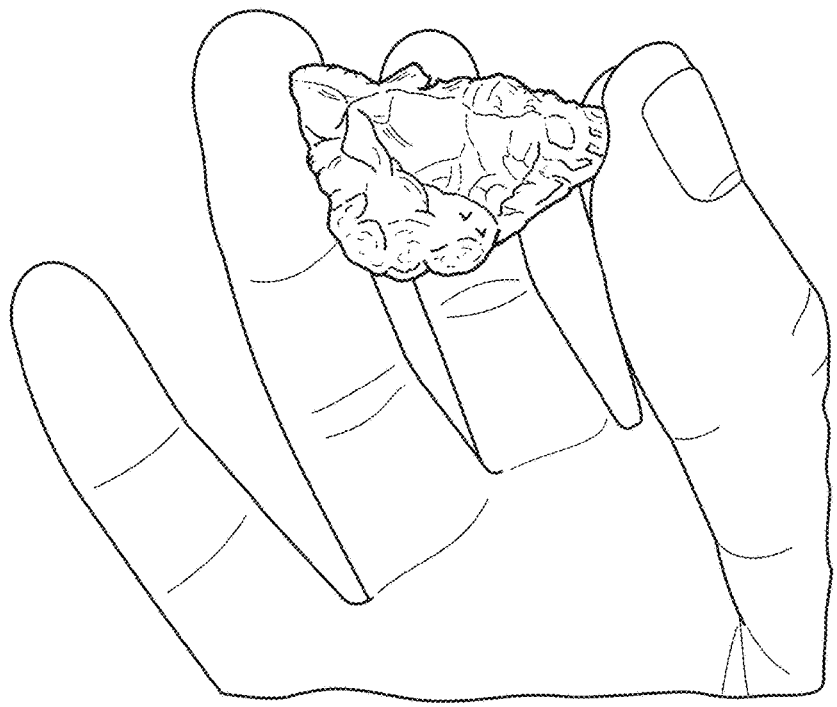
FIG. 6 illustrates a picture of casein glue according to an embodiment of the present invention.

Method 4:

In one embodiment, a method of coating pills using casein glue is disclosed. The casein glue, shown in FIG. 6, can be utilized to create uniformly coated pills. The casein glue is prepared by mixing water, casein, caseinate, hydrated lime solution and sodium silicate. The mixture is stirred or homogenized to form a wet-mix glue. The glue is rich in water, however, some of its components readily absorb moisture. Alternatively, water-rich glue can be utilized as coating in its present aggregate state, or dried and used as powder coating, or with combination of pre-mentioned embodiments. Alternatively, the casein glue is baked and used as a wrap to enclose the pill.

Figure 7:
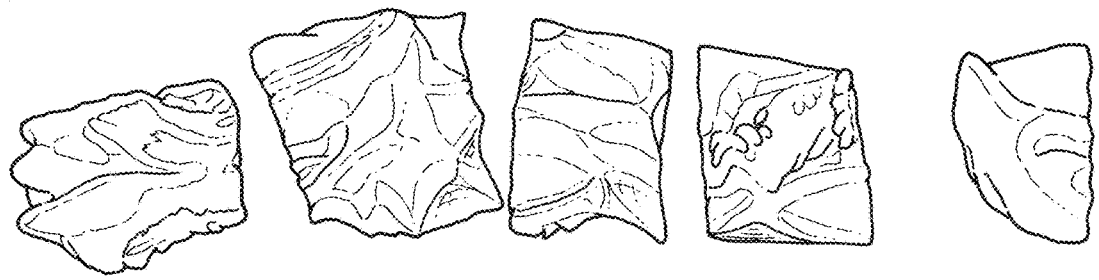
FIG. 7 illustrates a picture of casein clay according to an embodiment of the present invention.
Figure 7:
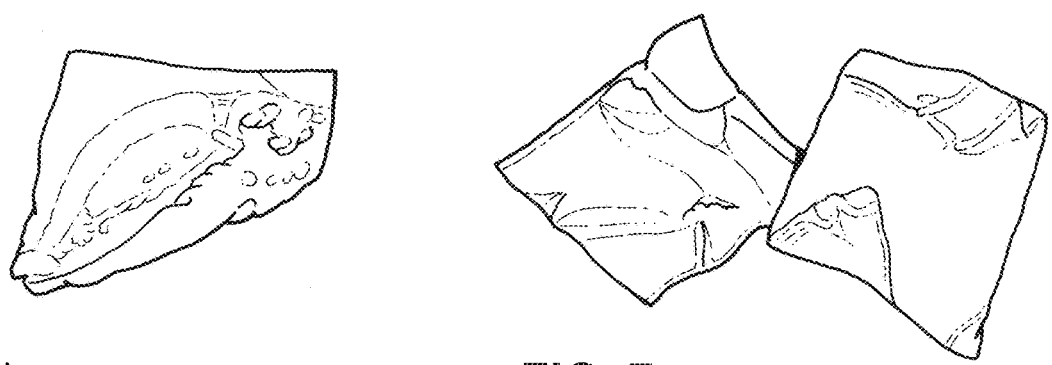

Method 5:

In one embodiment, a method of producing casein clay is disclosed. In one embodiment, the method involves blending of modified casein with oleic acid and modifying the pH in the weak base range to form clay. The casein clay could be wrapped around the pill. In one embodiment, the casein clay comprising 5 to 20 grams of modified casein mixture is dispersed under 50 ml of basic water (by adding NaOH). After an hour of stirring, up to 20 wt. % of oleic acid is added. Then, some silica and talc (6 to 9 wt. %) is introduced (optional) followed by 2 hours of stirring. The resulting casein clay, shown in FIG. 7, could be molded or thinned to desired film thicknesses and then enwrapment can be achieved immediately.

Advantageously, the composition could be used in application such as band-aids, surgical pads, self-curing gel, post baby delivery cooling pad, breast feeding bras, gym sweat pads, military vests, daily use pads (panty-liners), sanitary pads and tampons. Further, the composition could be used in any application that requires indication of overflow of fluid.

Although a single embodiment of the invention has been illustrated in the accompanying drawings and described in the above detailed description, it will be understood that the invention is not limited to the embodiment developed herein, but is capable of numerous rearrangements, modifications, substitutions of parts and elements without departing from the spirit and scope of the invention.

The foregoing description comprises illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A system for producing a sensory stimulation, comprising:
   at least one of a sanitary pad, a panty-liner, a military vest or a band-aid comprising a sensory stimulant composition; wherein the sensory stimulant composition includes;
   at least one cooling agent, wherein the cooling agent comprises urea and/or ammonium nitrate;
   modified casein;
   one or more fillers;
   one or more colorants;
   one or more carbohydrates, and
   one or more pharmaceutically acceptable salts, wherein the salt comprises potassium chloride, wherein the modified casein coats the sensory stimulant composition so that the sensory stimulant composition is configured to dissolve in blood, and the sensory stimulant composition produces a temperature drop on a surrounding environment upon exposure to the blood.

2. A method for producing a sensory stimulation, comprising:
   providing on at least one of a sanitary pad, a panty-liner, a military vest or a band-aid aid comprising a sensory stimulant composition, wherein the sensory stimulant composition includes at least one cooling agent, wherein the cooling agent comprises urea and/or ammonium nitrate, modified casein, one or more fillers, one or more colorants, one or more carbohydrates, and one or more pharmaceutically acceptable salts, wherein the salt comprises potassium chloride, wherein the modified casein coats the sensory stimulant composition so that the sensory stimulant composition is configured to dissolve in blood;
   dissolving the sensory stimulant composition when the sensory stimulant composition interacts with blood;
   producing a temperature drop on an environment surrounding the sensory stimulant composition of the at least one at least one of the sanitary pad, the panty-liner, the military vest or the band-aid upon the sensory stimulant composition being exposed to the blood.

* * * * *